(12) United States Patent
Johansson et al.

(10) Patent No.: US 8,148,492 B2
(45) Date of Patent: Apr. 3, 2012

(54) SYNTHETIC PULMONARY SURFACTANT PEPTIDES

(75) Inventors: Jan Johansson, Stockholm (SE); Tore Curstedt, Sollentuna (SE); Bengt Robertson, Stockholm (SE); Maurlzio Delcanale, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 454 days.

(21) Appl. No.: 12/222,517

(22) Filed: Aug. 11, 2008

(65) Prior Publication Data

US 2009/0075892 A1    Mar. 19, 2009

(30) Foreign Application Priority Data

Aug. 9, 2007  (EP) .................................... 07114083

(51) Int. Cl.
*C07K 14/00* (2006.01)
(52) U.S. Cl. ......... 530/324; 514/15; 514/15.5; 514/21.3
(58) Field of Classification Search .................. 530/324; 514/15, 15.5, 21.3
See application file for complete search history.

(56) References Cited

U.S. PATENT DOCUMENTS

| 2008/0242589 A1 | 10/2008 | Curstedt et al. |
| 2009/0088379 A1 | 4/2009 | Johansson et al. |

FOREIGN PATENT DOCUMENTS

| WO | 02/28368 | 4/2002 |
| WO | 02/28377 | 4/2002 |
| WO | 02/28378 | 4/2002 |

OTHER PUBLICATIONS

Razzetti, R., et al., "Formoterol and Beclomethasone Dipropionate Interact Positively in Antagonising Bronchoconstriction and Inflammation in the Lung," Pharmacological Research, vol. 55, 2007, pp. 426-432.
Bouros, D., et al., "Formoterol and Beclomethasone Versus Higher Dose Beclomethasone as Maintenance Therapy in Adult Asthma," Eur Respir J, vol. 14, 1999, pp. 627-632.
U.S. Appl. No. 12/422,581, filed Apr. 13, 2009, Johansson, et al.

*Primary Examiner* — David Lukton
(74) *Attorney, Agent, or Firm* — Oblon, Spivak, McClelland, Maier & Neustadt, L.L.P.

(57) ABSTRACT

The present invention is directed to a reconstituted surfactant comprising a lipid carrier, a polypeptide analog of the native surfactant protein SP-C, and a polypeptide analog of the native surfactant protein SP-B. The invention is also directed to the pharmaceutical compositions thereof and to a use thereof in the treatment or prophylaxis of RDS and other respiratory disorders.

38 Claims, 1 Drawing Sheet

Figure 1

```
Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
            35                  40                  45

Leu Ala Glu Arg Tyr Ser Val Ile Leu Asp Thr Leu Leu Gly Arg
    50                  55                  60

Met Leu Pro Gln Leu Val Cys Arg Leu Val Leu Arg Cys Ser Met
65                  70                  75
```

SYNTHETIC PULMONARY SURFACTANT PEPTIDES

CROSS-REFERENCE TO RELATED APPLICATIONS

The present application claims priority to EP 07114083.4, filed on Aug. 9, 2007, which is incorporated herein by reference in its entirety.

BACKGROUND OF THE INVENTION

1. Field of the Invention

The present invention provides peptides analogues of the native surfactant protein SP-B and their use in the preparation of formulations for the prophylaxis and/or treatment of respiratory distress syndrome (RDS) and other respiratory disorders.

2. Discussion of the Background

The human lung is composed of a large number of small air sacs, called alveoli, in which gases are exchanged between the blood and the air spaces of the lungs. In healthy individuals, this exchange is mediated by the presence of a protein-containing surfactant complex that prevents the lungs from collapsing at the end of expiration.

Lung surfactant complex is composed primarily of lipid and contains minor amounts of various proteins. An absence of adequate levels of this complex results in malfunction of the lung. This syndrome is called Respiratory Distress Syndrome (RDS) and it commonly affects preterm infants.

Said syndrome is effectively treated with modified natural surfactant preparations extracted from animal lungs.

The main constituents of these surfactant preparations are phospholipids, such as 1,2-dipalmitoyl-sn-glycero-3-phosphocholine commonly known as dipalmitoyl-phosphatidyl-choline (DPPC), phosphatidylglycerol (PG) and surfactant hydrophobic proteins B and C (SP-B and SP-C) that are known to have the capacity to effect the surfactant-like activity of said preparations.

Due to the drawbacks of the surfactant preparations from animal tissues, such as the complication of the production and sterilization processes and possible induction of immune reactions, synthetic surfactants mimicking the composition of the modified natural surfactants have been developed.

Said synthetic surfactants are known as reconstituted surfactants.

However the development of clinically active reconstituted surfactants turned out to be complicated as the isolation of significant amounts of hydrophobic SP-B and SP-C proteins from natural sources is both expensive and labor intensive.

Likewise, production of these proteins by recombinant DNA techniques requires substantial effort in terms of design and achieving optimal host/vector expression systems. In addition, considerable effort is required to develop effective isolation strategies to separate and purify the expressed protein of interest from the unwanted material.

In particular the SP-B protein is characterised by high molecular weight, extreme hydrophobicity and a large number of cysteine residues which markedly complicates its commercial production via isolation from natural materials or its expression via recombinant DNA strategies.

Therefore the medical community has a need for simple, easy-to-prepare, synthetic analogues of the protein SP-B able of mimicking all the properties of the native protein.

More particularly there is a need of synthetic analogues of the protein SP-B that, when admixed with synthetic analogues of the native protein SP-C and with a lipid carrier, give rise to reconstituted surfactant preparations able of efficaciously maintaining alveolar patency at the end of expiration.

SUMMARY OF THE INVENTION

It is an object of the present invention to provide a polypeptide comprising the sequence represented by formulae (I) or (II)

XΔLCRALIKRFNRYLTPQLVCRLVLRΦΣ$_n$  (I; SEQ ID NO: 1)

XΔLCRALIKRYNGKPQLVCRLVLRΦΣ$_n$  (II; SEQ ID NO: 6)

wherein
X is an amino acid residue independently selected from the group consisting of C, A, G, K, R, D and E;
Δ is an amino acid residue selected from the group consisting of W, L, nL and I;
Φ is an amino acid residue independently selected from the group consisting of C, A, G, K, R, D and E
Σ$_n$ is an amino acid residue selected from the group consisting of S, G and A with a frequency represented by n
n is an integer having a value of 0 or 1.

It is also an object of the present invention to provide pharmaceutically acceptable salts of said polypeptides and their blocked N- and/or C-terminus derivatives, e.g via acetylation and amidation.

It is another object of the present invention to provide a reconstituted pulmonary surfactant comprising a lipid carrier admixed with a polypeptide of general formulae (I) and/or (II) and pharmaceutical formulations thereof.

It is still another object of the present invention to provide a use of the polypeptides of general formulae (I) and/or (II) for the preparation of a reconstituted surfactant for the prophylaxis and/or treatment of respiratory distress syndrome and other respiratory disorders.

The above objects highlight certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily obtained as the same becomes better understood by reference to the following Figures in conjunction with the detailed description below.

FIG. 1 shows the amino acid sequence of human protein SP-B (SEQ ID NO: 11).

DETAILED DESCRIPTION OF THE INVENTION

Unless specifically defined, all technical and scientific terms used herein have the same meaning as commonly understood by a skilled artisan in enzymology, biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The respiratory function after in vivo treatment with the exogenous surfactant preparations is determined by measuring two parameters: i) the tidal volume which is an index of the lung compliance and ii) the lung gas volume which is an index of the alveolar air expansion or patency at the end of expiration, and hence of the capability of forming a stable phospholipidic film in the alveoli at the end of expiration.

The protein SP-B, which has also been defined as "SP18", is a 17 k Da dimeric protein wherein the monomeric chain is a 79 residue polypeptide and has three intrachain disulfide linkages, linking Cys8 to Cys77, Cys11 to Cys71, and Cys35 to Cys46. In its native form, the human SP-B subunit exists as a disulfide-linked homodimer having an interchain disulfide linkage at Cys 48. The sequence of the monomeric chain of human SP-B is reported in Figure.

The term "reconstituted surfactant", as used herein, means a lipid carrier to which polypeptide analogues of the surfactant proteins, made through recombinant technology or synthetic methods have been added.

The term "lipid carrier" means a mixture of phosholipids and optionally further lipid components, for example neutral lipids such as triacylglycerols, free fatty acids and/or cholesterol.

The terms "polypeptide" and "peptide" are used interchangeably herein to designate a linear series of no more than about 60 amino acid residues connected one to the other by peptide bonds between the alpha-amino and carboxy groups of adjacent residues.

The term "polypeptide analogues of the native surfactant protein SP-B", includes peptides having an amino acid sequence in which, compared to the native proteins, one or more amino acids are missing or have been replaced by other amino acids so long as the polypeptides, in a mixture with a lipid carrier, show pulmonary surfactant activity.

The term "polypeptides analogues of the native surfactant protein SP-C", includes polypeptides having an amino acid sequence in which, compared to the native proteins, one or more amino acids are missing or have been replaced by other amino acids, so long as the polypeptides, in a mixture with a lipid carrier, show pulmonary surfactant activity.

Polypeptides displaying conservative substitutions are those where one amino acid residue is replaced by another, biologically similar residue. Examples of conservative substitutions include the substitution of one hydrophobic residue such as isoleucine, valine, leucine or methionine for another, or the substitution of one polar residue for another such as between arginine and lysine, or between glutamic and aspartic acids.

The term "conservative substitution" also includes the use of a substituted amino acid in place of an unsubstituted parent amino acid provided that the resulting polypeptide also displays the required surfactant activity.

Moreover, the term "conservative substitution" includes substitutions different from the previous ones, provided that the resulting polypeptide maintains the secondary structure as well as the required surfactant activity of the parent polypeptide.

The amino acid sequences are shown according to the three-letter code with the amino acid which carries the free amino group at the left end (amino terminus) and the amino acid which carries the free carboxyl group at the right end (carboxy terminus).

All the amino acid residues identified herein are in the natural L-configuration and the sequences identified herein are reported according to standard abbreviations for amino acid residues as shown in the following Table of Correspondence.

| TABLE OF CORRESPONDENCE | | |
|---|---|---|
| | SYMBOL | |
| AMINO ACID | One-letter | Three-letter |
| Glycine | G | Gly |
| L-proline | P | Pro |
| L-isoleucine | I | Ile |
| L-leucine | L | Leu |
| L-tyrosine | Y | Tyr |
| L-cysteine | C | Cys |
| L-tryptophane | W | Trp |
| L-alanine | A | Ala |
| L-lysine | K | Lys |
| L-arginine | R | Arg |
| L-glutamine | Q | Glu |
| L-methionine | M | Met |
| L-serine | S | Ser |
| L-valine | V | Val |
| L-aspargine | N | Asn |
| L-aspartic acid | D | Asp |
| L-glutamic acid | E | Gln |
| L-histidine | H | His |
| L-threonine | T | Thr |
| L-phenylalanine | F | Phe |
| L-nor-leucine | — | nLeu |
| L-ornithine | — | Orn |

The present invention is directed to a polypeptide comprising the sequence represented by formulae (I) or (II)

XΔLCRALIKRFNRYLTPQLVCRLVLRΦ$\Sigma_n$    (I; SEQ ID NO: 1)

XΔLCRALIKRYNGKPQLVCRLVLRΦ$\Sigma_n$    (II; SEQ ID NO: 6)

wherein
X is an amino acid residue independently selected from the group consisting of C, A, G, K, R, D and E;
Δ is an amino acid residue selected from the group consisting of W, L, nL and I;
Φ is an amino acid residue independently selected from the group consisting of C, A, G, K, R, D and E
$\Sigma_n$ is an amino acid residue selected from the group consisting of S, G and A with a frequency represented by n
n is an integer having a value of 0 or 1.

The polypeptides of the invention include the N-terminal sequence 8-17 and the C-terminal sequence 67-78 of SP-B protein linked through an amino acid sequence capable of forming a turn motif selected from the group consisting of FNRYLT (residues 11-16 of SEQ ID NO: 1) and YNGK (residues 11-14 of SEQ ID NO: 6).

Said polypeptides also include modifications such as those encompassed by the general formulae (I) or (II) wherein some of the amino acid residues of the sequences of native SP-B protein have been replaced and/or are missing.

Otherwise they may further include additional amino acid residues at the amino- or carboxy-terminal end. Said modifications may serve to enhance expression of the polypeptide or may serve as a "linker" sequence, but preferably do not decrease or otherwise interfere with the biological activity of a polypeptide of the present invention.

The invention also includes the pharmaceutically acceptable salts of said polypeptides and their blocked N- and/or C-terminus derivatives, e.g via acetylation and amidation.

Pharmaceutically acceptable salts include for example, salts of hydrochloric acid, acetic acid, and trifluoroacetic acid.

In one embodiment, the polypeptides of general formulae (I) or (II) may be in the form of disulfide linked molecule wherein the intramolecular disulfide linkage is between the Cys residue at position 4 and the one in the C-terminal part.

A first group of preferred polypeptides are those of general formulae (I) in which
X and Φ are both C;
Δ is as defined above; and
n is 0.

Advantageously said polypeptides may be in the form of disulfide linked molecule wherein the intramolecular disulfide linkage is between the two Cys residues at position 1 and 27 and/or between the two Cys residues at position 4 and 21.

A second group of preferred polypeptides are those of general formula (II) in which
X and Φ are both C;
Δ is as defined above; and
n is 0 or 1.

Advantageously, said polypeptides may be in the form of disulfide linked molecule wherein the intramolecular disulfide linkage is between the two Cys residues at position 1 and 25 and/or between the two Cys residues at position 4 and 19.

A third group of preferred polypeptides are those of general formula (I) in which
X is A or G;
Δ is as defined above;
n is 0 or 1; and
Φ is A or G.

Advantageously, said polypeptides may be in the form of cyclic molecule wherein the intramolecular linkage is between the Ala or the Gly residues at positions 1 and 27. More advantageously a disulfide linkage is also present between the two Cys residues at positions 4 and 21.

A fourth group of preferred polypeptides compounds are those of general formula (II) in which
X is A or G;
Δ is as defined above;
n is 0 or 1; and
Φ is A or G.

Advantageously, said polypeptides may be in the form of cyclic molecule wherein the intramolecular linkage is between the Ala or the Gly residues at positions 1 and 25. More advantageously, a disulfide linkage is also present between the two Cys residues at positions 4 and 19.

A fifth group of preferred polypeptides are those of general formula (I) in which
X is K or R;
Δ is as defined above;
n is 0 or 1; and
Φ is D or E.

Advantageously, said polypeptides may be in the form of cyclic molecule wherein the linkage is between the K or R residue at position 1 and the D or E residue at position 27. The linkage may be in form of amide covalent bond between the free amino group of the K or R residue and the free carboxylic group of the D or E residue, otherwise the linkage may be under the form of salt bridge. More advantageously, a disulfide linkage is also present between the two Cys residues at positions 4 and 21.

A sixth group of preferred polypeptides compounds are those of general formula (II) in which
X is K or R;
Δ is as defined above;
n is 0 or 1; and
Φ is D or E.

Advantageously, said polypeptides may be in the form of cyclic molecule wherein the linkage is between the K or R residue at position 1 and the D or E residue at position 25. The linkage may be in form of amide covalent bond between the free amino group of the K or R residue and the free carboxylic group of the D or E residue, otherwise the linkage may be under the form of salt bridge. More advantageously, a disulfide linkage is also present between the two Cys residues at positions 4 and 19.

A seventh group of preferred polypeptides are those of general formula (I) in which
X is D or E;
Δ is as defined above;
n is 0 or 1; and
Φ is K or R.

Advantageously, said polypeptides may be in the form of cyclic molecule wherein the linkage is between the D or E residue at position 1 and the K or R residue at position 27. The linkage may be in form of amide covalent bond between the free amino group of the K or R residue and the free carboxylic group of the D or E residue, otherwise the linkage may be under the form of salt bridge. More advantageously, a disulfide linkage is also present between the two Cys residues at positions 4 and 21.

A eighth group of preferred polypeptides compounds are those of general formula (II) in which
X is D or E;
Δ is as defined above;
n is 0 or 1; and
Φ is K or R.

Advantageously, said polypeptides may be in the form of cyclic molecule wherein the linkage is between the D or E residue at position 1 and the K or R residue at position 25. The linkage may be in form of amide covalent bond between the free amino group of the K or R residue and the free carboxylic group of the D or E residue, otherwise the linkage may be under the form of salt bridge. More advantageously a disulfide linkage is also present between the two Cys residues in positions 4 and 19.

Preferred polypeptides encompassed by general formula (I) include:

```
CLLCRALIKRFNRYLTPQLVCRLVLRC;      (SEQ ID NO: 2)

CWLCRALIKRFNRYLTPQLVCRLVLRC;      (SEQ ID NO: 3)

ALLCRALIKRFNRYLTPQLVCRLVLRAA;     (SEQ ID NO: 4)
and

GLLCRALIKRFNRYLTPQLVCRLVLRGG.     (SEQ ID NO: 5)
```

Preferred polypeptides encompassed by general formula (II) include:

```
CLLCRALIKRYNGKPQLVCRLVLRC;        (SEQ ID NO: 7)

CWLCRALIKRYNGKPQLVCRLVLRC;        (SEQ ID NO: 8)

ALLCRALIKRYNGKPQLVCRLVLRAA;       (SEQ ID NO: 9)
and

GLLCRALIKRYNGKPQLVCRLVLRGG.       (SEQ ID NO: 10)
```

The polypeptides of SEQ ID NO: 3 and SEQ ID NO: 8 in the form of disulfide linked molecules wherein the intramolecular disulfide linkages are between the Cys residues are hereinafter indicated as ox-(Ic) and ox-(Id) polypeptides.

The polypeptides of the invention, when admixed with a lipid carrier comprising phospholipids, form a reconstituted surfactant able of reducing the surface tension to values near zero.

The present inventors have also discovered that, in a model of RDS wherein the immature newborn were treated without applying a positive end expiratory pressure (PEEP), the polypeptides of the present invention, when admixed with particular synthetic analogues of the protein SP-C and with a suitable lipid carrier, improve the respiratory function as expressed by the tidal volumes to an extent comparable with that achieved after administration of a modified natural surfactant.

Moreover, said reconstituted surfactant preparation turned out to improve the lung gas volume which is an index of the alveolar patency at the end of expiration.

The polypeptides of general formulae (I) and/or (II) may be synthesized by any techniques that are known to those skilled in the polypeptide art.

Many of the techniques available may be found in J. M. Steward and J. D. Young, "Solid Phase Peptide Synthesis", W.H. Freeman Co., San Francisco, 1969, and J. Meienhofer, Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis. The polypeptides of the invention may also be prepared using the solid-phase synthetic technique initially described by Merrifield, in J. Am. Chem. Soc. 85: 2149-2154 (1963). Other polypeptide synthesis techniques may be found, for example, in M. Bodanszky et al., Peptide Synthesis, John Wiley & Sons, 2d Ed., (1976) as well as in other reference works known to those skilled in the art.

Appropriate protective groups for use in such syntheses will be found in the above texts as well as in J. F. W. McOmie, Protective Groups in Organic Chemistry, Plenum Press, New York, N.Y. (1973).

In general, these methods comprise the sequential addition of one or more amino acid residues or suitably protected amino acid residues to a growing peptide chain.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth.

After all the desired amino acids have been linked in the proper sequence, any remaining terminal and side group protecting groups (and solid support) are removed sequentially or concurrently, to give rise to the final polypeptide.

The raw polypeptide is generally purified by HPLC and isolated by lyophilisation.

The polypeptide may be obtained in the form of pharmaceutically acceptable salt. Optionally the obtained salt may be converted in another type of salt using a column packed with a suitable ion exchange resin according to a procedure well-known to a skilled person.

The polypeptides of the invention may also be prepared using recombinant nucleic acid methodologies well known in the art.

Therefore the DNA sequences coding the polypeptides of the invention, the recombinant expression vectors capable of expressing them and methods thereof are included in the present invention.

A DNA sequence coding for a polypeptide of this invention may be synthesized by chemical techniques well known to the skilled person. The DNA segment may then be ligated into an expression vector, and a host transformed therewith may be used to produce the polypeptide.

By chemically synthesizing the coding sequence, any desired modifications may be made simply by substituting the appropriate bases for those encoding the native amino acid residue sequence.

The recombinant expression vectors capable of expressing a subject polypeptide and methods of their use for producing the polypeptides of general formulae (I) and/or (II) are included in the present invention.

Also included in the present invention are ribonucleic acid (RNA) equivalents of the above described DNA segments.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences may code for a particular amino acid residue sequence. Such nucleotide sequences are considered functionally equivalent since they may result in the production of the same amino acid residue sequence in all organisms.

The polypeptides of general formulae (I) and/or (II) may be admixed with a pharmaceutically acceptable lipid carrier to form a reconstituted surfactant.

The weight ratios between the polypeptide and the lipid carrier is advantageously in the range of about 1:5 to about 1:5000, preferably about 1:10 to about 1:2000, and more preferably about 1:50 to about 1:1000. In a more preferred embodiment, the polypeptide:lipid carrier weight ratio is in the range of about 1:5 to about 1:1000, preferably about 1:7 to about 1:500, and more preferably about 1:10 to about 100.

Advantageously, the lipid carrier comprises the phospholipids that are contained in natural pulmonary surfactant preparations, for example phosphatidylcholines (PC) such as dipalmitoylphosphatidylcholine (DPPC) and palmitoyloleoylphosphatidylcholine (POPC), and phosphatidylglycerols (PG), such as palmitoyloleoylphosphatidylglycerol (POPG) and dipalmitoylphosphatidylglycerol (DPPG).

Other phospholipids which can be advantageously used are phosphatidylinositols (PI), phosphatidylethanolamines (PE), phosphatidylserines and sphingomyelins (SM).

In a particular embodiment, the lipid carrier may comprise further components, for example neutral lipids such as triacylglycerols, free fatty acids and/or cholesterol.

The reconstituted surfactant may comprise one or more polypeptides of formulae (I) and/or (II) or may further comprise a synthetic peptide analogue of the native surfactant protein SP-C such as those disclosed in WO 95/32992, WO 00/47623, and WO 03/097695.

Reconstituted surfactants comprising a polypeptide of the invention may be prepared by mixing a solution or a suspension of said polypeptide, optionally a solution or a suspension of another peptide and the lipid carrier, then by subsequently drying the mixture.

Otherwise they may be prepared by lyophilisation or spray-drying according to methods known in the art.

The administration of said reconstituted surfactant preparation may be carried out in a manner known to the person skilled in the art, preferably by intratracheal installation (infusion or bolus). Otherwise the administration may be carried out by aerosolization or by nebulisation.

The present invention also concerns pharmaceutical compositions including the reconstituted surfactant comprising the polypeptides of the invention.

Said compositions are advantageously administered in the form of a solution, dispersion, suspension or dry powder.

Preferably said compositions comprise the reconstituted surfactant dissolved or suspended in a suitable solvent or resuspension medium.

Preferably said pharmaceutical compositions are supplied as suspension in a buffered physiological saline aqueous solution in single-use glass vials. Advantageously the reconstituted surfactant concentration (expressed as phospholipid content) is in the range of from about 2 to about 160 mg of surfactant per ml, preferably between 10 and 100 mg/ml, more preferably between 20 and 80 mg/ml.

Said compositions may further comprise electrolytes, such as calcium, magnesium and/or sodium salts (for example calcium chloride or sodium chloride).

The compositions in the form of aqueous suspension may also be administered by nebulisation.

If it is to be used in aerosol administration, the reconstituted surfactant is supplied in finely divided form along with a propellant. Useful propellants are typically gases at ambient conditions that are condensed under pressure. such as hydrofluoroalkanes.

The aerosol is packaged in a container equipped with a suitable valve so that the ingredients may be maintained under pressure until released.

The pharmaceutical compositions obtained with the polypeptides of the invention are suitable for the treatment or prophylaxis of respiratory distress syndrome (RDS) in prematurely born babies or in the treatment or prophylaxis of other diseases related to a surfactant-deficiency or dysfunction including RDS in adults (ARDS), meconium aspiration syndrome (MAS), and bronchopulmonary dysplasia (BPD).

They may also be useful for the treatment or prophylaxis of other respiratory disorders such as pneumonia, bronchitis, COPD (chronic obstructive pulmonary disease), asthma, and cystic fibrosis as well as for the treatment of serous otitis media (glue ear).

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Example 1

Synthesis and Purification of the Polypeptide ox-(Ic)

The polypeptide ox-(Ic) was prepared by standard SPPS (Solid Phase Peptide Synthesis) methods based on Fmoc chemistry, according to the Scheme 1 reported below.

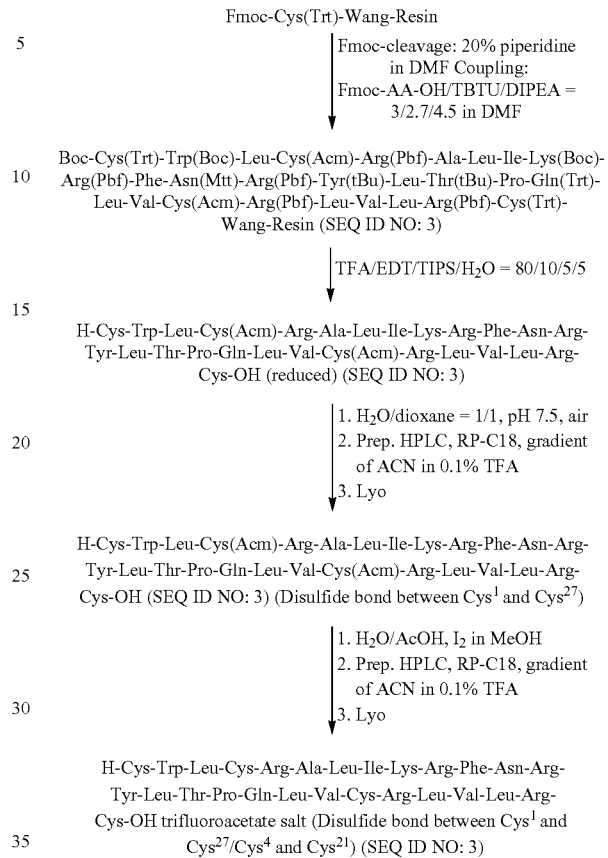

After the solid phase synthesis, the crude peptide without disulfide bridges was cleaved from the resin by standard methods, then the disulfide bridges were formed selectively by two different oxidation steps.

To selectively form the disulfide bridges, a defined protection pattern for the lateral groups of the four cysteines was chosen during the synthesis. In the process showed in the Scheme 1, $Cys^1$ and $Cys^{27}$ were introduced as Fmoc-Cys(Trt)-OH during SPPS, whereas $Cys^4$ and $Cys^{21}$ were coupled as the corresponding Acm-derivatives.

The first disulfide bridge was formed by air oxidation and the peptide having one bridge was purified by HPLC systems and isolated by lyophilisation. The second disulfide bridge was formed by iodine oxidation, and the final peptide was purified by HPLC system and isolated by lyophilisation.

The purity of the final polypeptide was checked by reversed phase high performance liquid chromatography (HPLC), using a $C_{18}$ column and turned out to be 92%.

Its molecular mass was determined by ESI-MS.

Yield: 1.73 g (2.4%).

Example 2

Synthesis and Purification of the Polypeptide ox-(Id)

The polypeptide ox-(Id) was prepared in a similar way according to the Scheme 2 reported below.

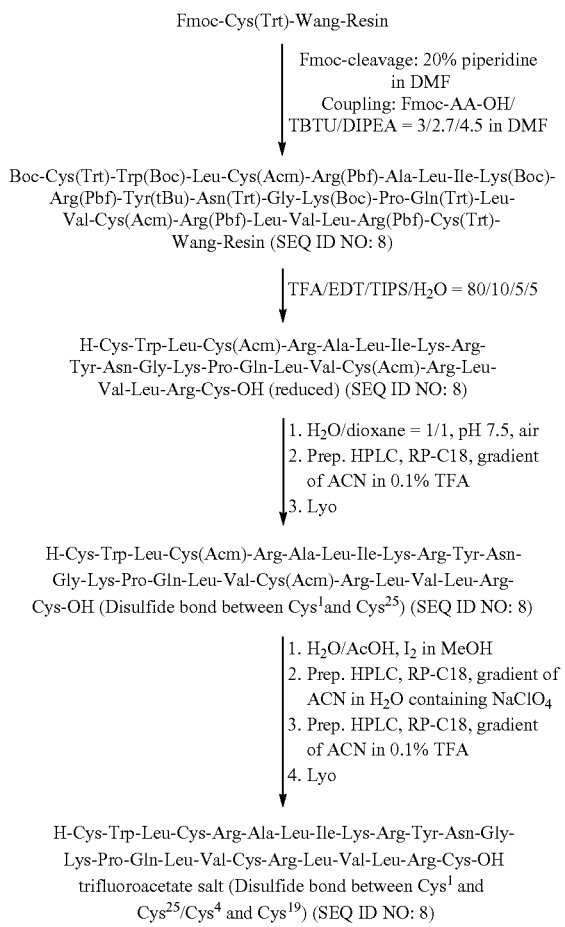

The introduction the disulfide bridges between $Cys^1$ and $Cys^{27}$ and between $Cys^4$ and $Cys^{21}$, the purification and the isolation were carried out as reported in the Example 1.

The purity of the final polypeptide was checked by reversed phase high performance liquid chromatography (HPLC), using a $C_{18}$ column and turned out to be 86%.

Its molecular mass was determined by ESI-MS.

Yield: 0.81 g (2.4%).

LEGEND

AA-OH Amino acid
ACN Acetonitrile
AcOEt Ethyl acetate
AcOH Acetic acid
Acm Acetamidomethyl
Boc t-Butyloxycarbonyl
n-BuOH n-Butanol
tBu t-Butyl
DIPEA N,N-Diisopropylethylamine
DMF N,N-Dimethylformamide
EDT 1,2-Ethanedithiol
ESI-MS Electrospray ionization-mass spectrometry
Fmoc 9-Fluorenylmethyloxycarbonyl
HPLC High-performance liquid chromatography
Lyo lyophilisation
Mtt Methyltrityl
PBF 2,2,4,6,7-Pentamethyl-2,3-dihydro-benzofuran-5-sulfonyl
SPPS Solid phase peptide synthesis
TBTU 2-(1H-Benzotriazol-1-yl)-1,1,3,3-tetramethyluronium tetrafluoroborate
TFA Trifluoroacetic acid
TIPS Triisopropylsilyl
Trt Trityl Numerous modifications and variations on the present invention are possible in light of the above teachings. It is, therefore, to be understood that within the scope of the accompanying claims, the invention may be practiced otherwise than as specifically described herein.

What we claim is:

1. An isolated polypeptide comprising the sequence represented by formula (I)

XΔLCRALIKRFNRYLTPQLVCRLVLRΦΣ$_n$  (I; SEQ ID NO: 1)

wherein
- X is an amino acid residue independently selected from the group consisting of C, A, G, K, R, D and E;
- Δ is an amino acid residue selected form the group consisting of W, L, nL and I;
- Φ is an amino acid residue independently selected from the group consisting of C, A, G, K, R, D and E
- Σ$_n$ is an amino acid residue selected from the group consisting of S, G and A with a frequency represented by n
- n is an integer having a value of 0 or 1.

2. The polypeptide of claim 1, wherein X and Φ are both C, and n is 0.

3. The polypeptide of claim 2, wherein said polypeptide is in the form of a disulfide linked molecule wherein the intramolecular disulfide linkage is between the two Cys residues at positions 1 and 27.

4. The polypeptide of claim 2, wherein said polypeptide is in the form of a disulfide linked molecule wherein the intramolecular disulfide linkage is between the two Cys residues at positions 4 and 21.

5. The polypeptide of claim 2, wherein said polypeptide is in the form of a disulfide linked molecule wherein the intramolecular disulfide linkage is between the two Cys residues at positions 1 and 27 and is between the two Cys residues at positions 4 and 21.

6. The polypeptide of claim 1, wherein X and Φ are both A or G.

7. The polypeptide of claim 1, wherein X is K or R, and Φ is D or E.

8. The polypeptide of claim 1, wherein X is D or E, and Φ is K or R.

9. The polypeptide of claim 1, wherein said polypeptide is selected from the group consisting of

| | |
|---|---|
| CLLCRALIKRFNRYLTPQLVCRLVLRC; | (SEQ ID NO: 2) |
| CWLCRALIKRFNRYLTPQLVCRLVLRC; | (SEQ ID NO: 3) |
| ALLCRALIKRFNRYLTPQLVCRLVLRAA; and | (SEQ ID NO: 4) |
| GLLCRALIKRFNRYLTPQLVCRLVLRGG. | (SEQ ID NO: 5) |

10. The polypeptide of claim 1, wherein said polypeptide is

CWLCRALIKRFNRYLTPQLVCRLVLRC.        (SEQ ID NO: 3)

11. The polypeptide of claim 10, wherein said polypeptide is in the form of a disulfide linked molecule wherein the intramolecular disulfide linkage is between the two Cys residues at positions 1 and 27.

12. The polypeptide of claim 10, wherein said polypeptide is in the form of a disulfide linked molecule wherein the intramolecular disulfide linkage is between the two Cys residues at positions 4 and 21.

13. The polypeptide of claim 10, wherein said polypeptide is in the form of a disulfide linked molecule wherein the intramolecular disulfide linkage is between the two Cys residues at positions 1 and 27 and is between the two Cys residues at positions 4 and 21.

14. A reconstituted surfactant which comprises a polypeptide of claim 1 in admixture with a lipid carrier.

15. The reconstituted surfactant of claim 14 further comprising a synthetic peptide analogue of the native surfactant protein SP-C.

16. The reconstituted surfactant of claim 14, wherein the lipid carrier comprises a mixture of phospholipids.

17. A method of treating respiratory distress syndrome (RDS) in prematurely born babies comprising administering to a subject in need thereof an effective amount of the reconstituted surfactant according to claim 14.

18. A method of treating a disease related to a surfactant-deficiency or dysfunction comprising administering to a subject in need thereof an effective amount of the reconstituted surfactant according to claim 14.

19. The method according to claim 18, wherein the disease related to a surfactant-deficiency or dysfunction is selected from the group consisting of RDS in adults (ARDS), meconium aspiration syndrome (MAS), and bronchopulmonary dysplasia (BPD).

20. An isolated polypeptide comprising the sequence represented by formula (II)

X$\Delta$LCRALIKRYNGKPQLVCRLVLR$\Phi\Sigma_n$,        (II; SEQ ID NO: 6)

wherein
X is an amino acid residue independently selected from the group consisting of C, A, G, K, R, D and E;
$\Delta$ is an amino acid residue selected from the group consisting of W, L, nL and I;
$\Phi$ is an amino acid residue independently selected from the group consisting of C, A, G, K, R, D and E
$\Sigma_n$ is an amino acid residue selected form the group consisting of S, G and A with a frequency represented by n
n is an integer having a value of 0 or 1.

21. The polypeptide of claim 20, wherein X and $\Phi$ are both C, and n is 0.

22. The polypeptide of claim 20, wherein said polypeptide is in the form of a disulfide linked molecule wherein the intramolecular disulfide linkage is between the two Cys residues at positions 1 and 25.

23. The polypeptide of claim 20, wherein said polypeptide is in the form of a disulfide linked molecule wherein the intramolecular disulfide linkage is between the two Cys residues at positions 4 and 19.

24. The polypeptide of claim 20, wherein said polypeptide is in the form of a disulfide linked molecule wherein the intramolecular disulfide linkage is between the two Cys residues at positions 1 and 25 and is between the two Cys residues at positions 4 and 19.

25. The polypeptide of claim 20, wherein X and $\Phi$ are both A or G.

26. The polypeptide of claim 20, wherein X is K or R, and $\Phi$ is D or E.

27. The polypeptide of claim 20, wherein X is D or E, and $\Phi$ is K or R.

28. The polypeptide of claim 20, wherein said polypeptide is selected from the group consisting of

CLLCRALIKRYNGKPQLVCRLVLRC;      (SEQ ID NO: 7)

CWLCRALIKRYNGKPQLVCRLVLRC;      (SEQ ID NO: 8)

ALLCRALIKRYNGKPQLVCRLVLRAA;     (SEQ ID NO: 9)
and

GLLCRALIKRYNGKPQLVCRLVLRGG.     (SEQ ID NO: 10)

29. The polypeptide of claim 20, wherein said polypeptide is

CWLCRALIKRYNGKPQLVCRLVLRC.      SEQ ID NO: 8)

30. The polypeptide of claim 29, wherein said polypeptide is in the form of a disulfide linked molecule wherein the intramolecular disulfide linkage is between the two Cys residues at positions 1 and 25.

31. The polypeptide of claim 29, wherein said polypeptide is in the form of a disulfide linked molecule wherein the intramolecular disulfide linkage is between the two Cys residues at positions 4 and 19.

32. The polypeptide of claim 29, wherein said polypeptide is in the form of a disulfide linked molecule wherein the intramolecular disulfide linkage is between the two Cys residues at positions 1 and 25 and is between the two Cys residues at positions 4 and 19.

33. A reconstituted surfactant which comprises a polypeptide of claim 20 in admixture with a lipid carrier.

34. The reconstituted surfactant of claim 33 further comprising a synthetic peptide analogue of the native surfactant protein SP-C.

35. The reconstituted surfactant of claim 33, wherein the lipid carrier comprises a mixture of phospholipids.

36. A method of treating respiratory distress syndrome (RDS) in prematurely born babies comprising administering to a subject in need thereof an effective amount of the reconstituted surfactant according to claim 33.

37. A method of treating a disease related to a surfactant-deficiency or dysfunction comprising administering to a subject in need thereof an effective amount of the reconstituted surfactant according to claim 33.

38. The method according to claim 36, wherein the disease related to a surfactant-deficiency or dysfunction is selected from the group consisting of RDS in adults (ARDS), meconium aspiration syndrome (MAS), and bronchopulmonary dysplasia (BPD).

* * * * *

UNITED STATES PATENT AND TRADEMARK OFFICE
CERTIFICATE OF CORRECTION

PATENT NO.         : 8,148,492 B2
APPLICATION NO.    : 12/222517
DATED              : April 3, 2012
INVENTOR(S)        : Jan Johansson et al.

It is certified that error appears in the above-identified patent and that said Letters Patent is hereby corrected as shown below:

On the title page, Item (75), the fourth inventor's name is incorrect. Item (75) should read:

Item --(75) Inventor: Maurizio Delcanale, Parma (IT)--

Signed and Sealed this
Twenty-sixth Day of June, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,148,492 B2 | Page 1 of 1 |
| APPLICATION NO. | : 12/222517 | |
| DATED | : April 3, 2012 | |
| INVENTOR(S) | : Jan Johansson et al. | |

It is certified that error appears in the above-identified patent and that said Letters Patent is hereby corrected as shown below:

On the title page, Item (75), the fourth inventor's name is incorrect. Item (75) should read:

-- (75) Inventors: Jan Johansson, Stockholm (SE); Tore Curstedt, Sollentuna (SE); Bengt Robertson, Stockholm (SE); Maurizio Delcanale, Parma (IT)--

This certificate supersedes the Certificate of Correction issued June 26, 2012.

Signed and Sealed this
Eighth Day of January, 2013

David J. Kappos
*Director of the United States Patent and Trademark Office*

SEQUENCE LISTING

```
<160> NUMBER OF SEQ ID NOS: 11

<210> SEQ ID NO 1
<211> LENGTH: 28
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is an amino acid residue independently
      selected from the group consisting of C, A, G, K, R, D and E
<220> FEATURE:
<221> NAME/KEY: MISC_FEATURE
<222> LOCATION: (2)..(2)
<223> OTHER INFORMATION: X is an amino acid residue independently
      selected from the group consisting of W, L, nL and I
<220> FEATURE:
<221> NAME/KEY: MISC_FEATURE
<222> LOCATION: (27)..(27)
<223> OTHER INFORMATION: X is an amino acid residue independently
      selected from the group consisting of C, A, G, K, R, D and E
```

```
<220> FEATURE:
<221> NAME/KEY: MISC_FEATURE
<222> LOCATION: (28)..(28)
<223> OTHER INFORMATION: X is not present or is an amino acid residue
      independently selected from the group consisting of S, G and A

<400> SEQUENCE: 1

Xaa Xaa Leu Cys Arg Ala Leu Ile Lys Arg Phe Asn Arg Tyr Leu Thr
1               5                   10                  15

Pro Gln Leu Val Cys Arg Leu Val Leu Arg Xaa Xaa
            20                  25

<210> SEQ ID NO 2
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 2

Cys Leu Leu Cys Arg Ala Leu Ile Lys Arg Phe Asn Arg Tyr Leu Thr
1               5                   10                  15

Pro Gln Leu Val Cys Arg Leu Val Leu Arg Cys
            20                  25

<210> SEQ ID NO 3
<211> LENGTH: 27
<212> TYPE: PRT
<213> ORGANISM: Artificial Sequence
<220> FEATURE:
<223> OTHER INFORMATION: Synthetic Peptide

<400> SEQUENCE: 3

Cys Trp Leu Cys Arg Ala Leu Ile Lys Arg Phe Asn Arg Tyr Leu Thr
1               5                   10                  15

Pro Gln Leu Val Cys Arg Leu Val Leu Arg Cys
            20                  25

<210> SEQ ID NO 4
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 4

Ala Leu Leu Cys Arg Ala Leu Ile Lys Arg Phe Asn Arg Tyr Leu Thr
1               5                   10                  15

Pro Gln Leu Val Cys Arg Leu Val Leu Arg Ala Ala
            20                  25

<210> SEQ ID NO 5
<211> LENGTH: 28
<212> TYPE: PRT
<213> ORGANISM: Artificial Sequence
<220> FEATURE:
<223> OTHER INFORMATION: Synthetic Peptide

<400> SEQUENCE: 5

Gly Leu Leu Cys Arg Ala Leu Ile Lys Arg Phe Asn Arg Tyr Leu Thr
1               5                   10                  15

Pro Gln Leu Val Cys Arg Leu Val Leu Arg Gly Gly
            20                  25
```

```
<210> SEQ ID NO 6
<211> LENGTH: 26
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: X is an amino acid residue independently
      selected from the group consisting of C, A, G, K, R, D and E
<220> FEATURE:
<221> NAME/KEY: MISC_FEATURE
<222> LOCATION: (2)..(2)
<223> OTHER INFORMATION: X is an amino acid residue independently
      selected from the group consisting of W, L, nL and I
<220> FEATURE:
<221> NAME/KEY: MISC_FEATURE
<222> LOCATION: (25)..(25)
<223> OTHER INFORMATION: X is an amino acid residue independently
      selected from the group consisting of C, A, G, K, R, D and E
<220> FEATURE:
<221> NAME/KEY: MISC_FEATURE
<222> LOCATION: (26)..(26)
<223> OTHER INFORMATION: X is not present or is an amino acid residue
      independently selected from the group consisting of S, G and A

<400> SEQUENCE: 6

Xaa Xaa Leu Cys Arg Ala Leu Ile Lys Arg Tyr Asn Gly Lys Pro Gln
1               5                   10                  15

Leu Val Cys Arg Leu Val Leu Arg Xaa Xaa
            20                  25

<210> SEQ ID NO 7
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 7

Cys Leu Leu Cys Arg Ala Leu Ile Lys Arg Tyr Asn Gly Lys Pro Gln
1               5                   10                  15

Leu Val Cys Arg Leu Val Leu Arg Cys
            20                  25

<210> SEQ ID NO 8
<211> LENGTH: 25
<212> TYPE: PRT
<213> ORGANISM: Artificial Sequence
<220> FEATURE:
<223> OTHER INFORMATION: Synthetic Peptide

<400> SEQUENCE: 8

Cys Trp Leu Cys Arg Ala Leu Ile Lys Arg Tyr Asn Gly Lys Pro Gln
1               5                   10                  15

Leu Val Cys Arg Leu Val Leu Arg Cys
            20                  25

<210> SEQ ID NO 9
<211> LENGTH: 26
<212> TYPE: PRT
<213> ORGANISM: Artificial Sequence
<220> FEATURE:
<223> OTHER INFORMATION: Synthetic Peptide
```

-continued

```
<400> SEQUENCE: 9

Ala Leu Leu Cys Arg Ala Leu Ile Lys Arg Tyr Asn Gly Lys Pro Gln
1               5                   10                  15

Leu Val Cys Arg Leu Val Leu Arg Ala Ala
            20              25

<210> SEQ ID NO 10
<211> LENGTH: 26
<212> TYPE: PRT
<213> ORGANISM: Artificial Sequence
<220> FEATURE:
<223> OTHER INFORMATION: Synthetic Peptide

<400> SEQUENCE: 10

Gly Leu Leu Cys Arg Ala Leu Ile Lys Arg Tyr Asn Gly Lys Pro Gln
1               5                   10                  15

Leu Val Cys Arg Leu Val Leu Arg Gly Gly
            20              25

<210> SEQ ID NO 11
<211> LENGTH: 79
<212> TYPE: PRT
<213> ORGANISM: Homo sapiens

<400> SEQUENCE: 11

Phe Pro Ile Pro Leu Pro Tyr Cys Trp Leu Cys Arg Ala Leu Ile Lys
1               5                   10                  15

Arg Ile Gln Ala Met Ile Pro Lys Gly Ala Leu Ala Val Ala Val Ala
            20                  25                  30

Gln Val Cys Arg Val Val Pro Leu Val Ala Gly Gly Ile Cys Gln Cys
        35                  40                  45

Leu Ala Glu Arg Tyr Ser Val Ile Leu Leu Asp Thr Leu Leu Gly Arg
    50                  55                  60

Met Leu Pro Gln Leu Val Cys Arg Leu Val Leu Arg Cys Ser Met
65                  70                  75
```